United States Patent [19]

Wilk et al.

[11] Patent Number: 5,273,029

[45] Date of Patent: Dec. 28, 1993

[54] ENDOTRACHEAL TUBE ASSEMBLY AND RELATED METHOD AND OBTURATOR

[76] Inventors: Peter J. Wilk, 185 West End Ave., New York, N.Y. 10023; James Z. Cinberg, 167 N. Ridgewood Rd., South Orange, N.J. 07079

[21] Appl. No.: 876,516

[22] Filed: Apr. 30, 1992

[51] Int. Cl.$^5$ .............................................. A61M 16/00
[52] U.S. Cl. ........................... 128/200.26; 128/207.14
[58] Field of Search ................... 128/200.26, 205.23, 128/202.22, 207.14, 207.15, 780, 6, 768

[56] References Cited

U.S. PATENT DOCUMENTS

| | | | |
|---|---|---|---|
| 3,373,735 | 3/1968 | Gallagher | 128/768 |
| 4,691,701 | 9/1987 | Williams | 128/207.14 |
| 4,728,499 | 3/1988 | Fehder | 128/207.14 |
| 4,790,327 | 12/1988 | Despotis | 128/205.23 |
| 4,821,710 | 4/1989 | Greunwald et al. | 128/207.14 |
| 4,846,153 | 7/1989 | Berci | 128/6 |
| 4,879,999 | 11/1989 | Leiman et al. | 128/207.14 |
| 4,892,095 | 1/1990 | Nakhgevany | 128/200.26 |
| 4,928,687 | 5/1990 | Lampotang et al. | 128/200.26 |

FOREIGN PATENT DOCUMENTS 178028 11/1966 U.S.S.R. ............... 128/780

OTHER PUBLICATIONS

Mercury Medical Anesthesia Desk Reference, p. 59.

*Primary Examiner*—Edgar S. Burr
*Assistant Examiner*—Aaron J. Lewis
*Attorney, Agent, or Firm*—R. Neil Sudol; Henry D. Coleman

[57] ABSTRACT

An endotracheal assembly comprises an endotracheal tube, a malleable obturator inside the tube for enabling a placement of a distal end of the tube into a patient's trachea, and a colorimeteric carbon dioxide indicator mounted to the obturator for determining a passage of carbon dioxide through the tube upon a placement of the tube in the patient. The indicator may be removably connected to the obturator, for example, at the distal end thereof. In addition, cooperating locking elements are provided for releasably locking the indicator to the obturator.

14 Claims, 1 Drawing Sheet

ENDOTRACHEAL TUBE ASSEMBLY AND RELATED METHOD AND OBTURATOR

BACKGROUND OF THE INVENTION

This invention relates to an endotracheal tube placement assembly including an endotracheal tube and an obturator. This invention also relates to an associated method for placing an endotracheal tube with an obturator.

The dangers of improper endotracheal tube placement are well known and include death and disability. In an anesthetized patient, an endotracheal tube is placed to secure the air passageway and enable controlled oxygenation of the patient's lungs. However, if the distal end of the endotracheal tube is positioned in the esophagus rather than the lungs and the condition permitted to continue for even a short interval, brain injury and death can result.

It has been proposed to automatically or semiautomatically detect proper endotracheal tube placement by monitoring the carbon dioxide content of the gases escaping through a positioned endotracheal tube. U.S. Pat. Nos. 4,790,327 to Despotis, 4,821,710 to Greunwald et al., 4,879,999 to Leiman et al., 4,728,499 to Fehder, 4,691,701 to Williams, and 4,928,687 to Lampotang et al. disclose the use of colorimetric carbon dioxide indicators to determine the carbon dioxide content of gases exhaled through a positioned endotracheal tube. All the indicators are disposed at the proximal ends of endotracheal tubes, i.e. closest to the mouth and furthest from the lungs, or on devices connected to the proximal ends of endotracheal tubes. Accordingly, because carbon dioxide is present in exhaled air in a concentration of only 5%, the indicators must be especially sensitive to detect the carbon dioxide content of exhaled gases.

OBJECTS OF THE INVENTION

An object of the present invention is to provide an assembly for facilitating proper endotracheal tube placement.

Another object of the present invention is to provide a method for endotracheal tube placement which uses a carbon dioxide indicator to enable accurate positioning of an endotracheal tube.

Another, more particular, object of the present invention is to provide an endotracheal tube placement assembly with a carbon dioxide indicator which need not be as sensitive as indicators of prior art carbon dioxide indicators used in endotracheal tube placement.

A further particular object of the present invention is to provide an improved obturator for use in positioning an endotracheal tube.

SUMMARY OF THE INVENTION

An endotracheal assembly comprises, in accordance with the present invention, an endotracheal tube, a malleable obturator inside the tube for enabling a placement of a distal end of the tube into a patient's trachea, and a colorimeteric carbon dioxide indicator mounted to the obturator, particularly to the distal end thereof to ensure that the endotracheal tube is appropriately sited in the trachea and not in the esophagus.

The indicator may be removably connected or permanently attached to the distal end of the obturator. In the former case, cooperating locking elements may be provided on the obturator and an indicator member for releasably locking the indicator to the obturator.

Pursuant to another feature of the present invention, the obturator and the indicator are sterile, the endotracheal tube assembly further comprising a removable disposable wrapper enclosing the tube and the obturator for purposes of maintaining the tube, the obturator and the indicator in a sterile condition.

The obturator may be provided with a recess in which the indicator is permanently seated, while the indicator takes the form of a cylindrical strip surrounding a portion of the obturator.

A method for placing an endotracheal tube comprises, in accordance with the present invention, the steps of (a) initially inserting into a patient's trachea an endotracheal tube longitudinally traversed at least partially by an obturator made of a malleable material, (b) manipulating the tube and the obturator to effectuate a placement of the tube, (c) upon a placement of the tube with the obturator, withdrawing the obturator, and (d) inspecting a colorimeteric carbon dioxide indicator element mounted to a distal end of the obturator to determine the whether a distal end of the tube is properly placed in the patient.

According to another feature of the present invention, the method further comprises the steps of (e) removing the tube upon determining, via a color of the indicator element, that the tube is improperly placed, and (f) again inserting into the patient's trachea an endotracheal tube longitudinally traversed at least partially by an obturator made of a malleable material.

In the second insertion operation, the endotracheal tube and the obturator may be the same tube and obturator used in the step of initially inserting, provided that the indicator has not yet been exhausted and is still capable of registering a carbon dioxide presence. Alternatively, the obturator utilized in the subsequent insertion may be a different ("fresh") obturator. In the latter event, the endotracheal tube utilized in the subsequent placement attempt may be the same or a different tube from that used in the initial placement attempt. As yet another alternative, if the carbon dioxide indicator is separable from the obturator, a fresh indicator may be all that is needed to reinsert an endotracheal tube during a second placement attempt.

Naturally, if the color of the indicator at the distal end of the obturator evidences that the distal end of the endotracheal tube has been properly placed, the endotracheal tube may be permitted to remain in the patient's trachea for an extended duration.

An endotracheal tube placement assembly with a colorimetric carbon dioxide indicator on an obturator in accordance with the present invention is more reliable than existing devices wherein the carbon dioxide indicator is placed on the endotracheal tube. In those devices, the carbon dioxide indicator is necessarily disposed at the proximal end of the endotracheal tube, where the carbon dioxide is more dispersed and less concentrated than in the lungs.

DETAILED DESCRIPTION

Figure 1:
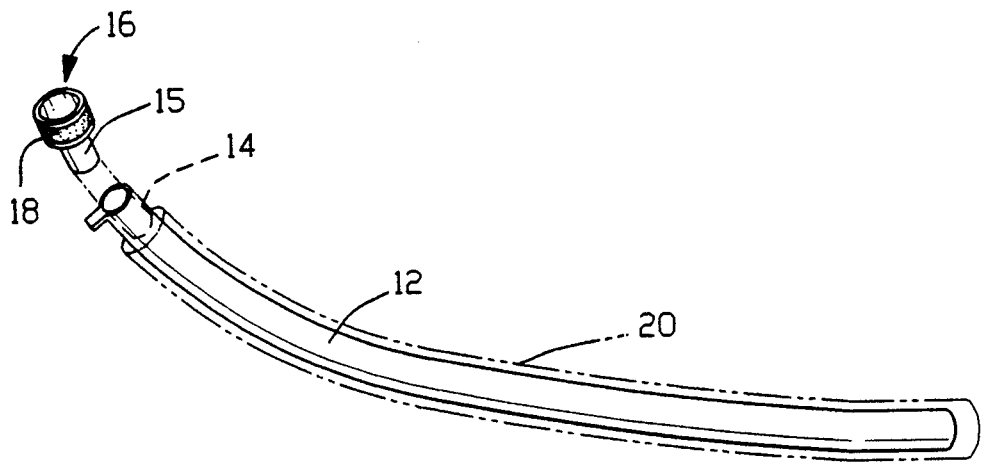
FIG. 1 is a schematic side perspective view of an endotracheal tube assembly in accordance with the present invention.

As illustrated in FIG. 1, an endotracheal tube assembly comprises a malleable obturator 12 proxided at a proximal end with a recess 14 for receiving a plug or finger element 15 of a indicator member 16. Indicator member 16 carries a colorimetric carbon dioxide indicator strip 18.

Obturator 12 is removably inserted into an endotracheal tube 20. The entire assembly may be contained in a sterile envelope or package (not shown) prior to use. Upon removal from the envelope or package, the endotracheal tube assembly of FIG. 1 is inserted into a patient's trachea in the same manner as conventional endotracheal tube assemblies. However, indicator strip 18 is monitored for color change to determine that the distal end of the endotracheal tube 20 has been properly positioned inside the patient's lung.

Figure 2:
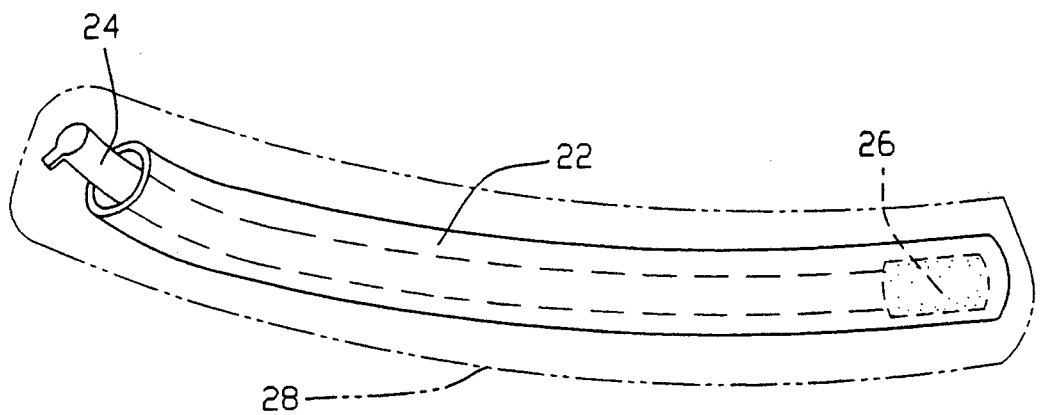
FIG. 2 is a schematic side perspective view of another endotracheal tube assembly in accordance with the present invention.

As depicted in FIG. 2, another endotracheal tube assembly comprises an endotracheal tube 22 in which a malleable tube placement obturator 24 is slidably disposed. Permanently attached to a distal end of obturator 24 is a colorimetric carbon dioxide indicator 26, for example, in the form of a strip inserted into an annular recess (not shown) in a distal end portion of obturator 24. Prior to use, tube 22 and obturator 24 are preserved in a sterile condition by a disposable envelope 28.

Figure 3:
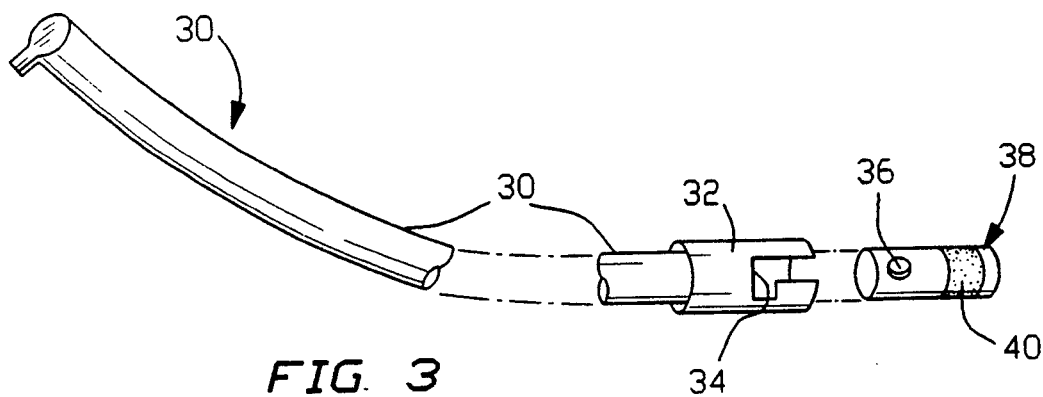
FIG. 3 is a schematic side perspective view of an obturator for use in an endotracheal tube assembly in accordance with the present invention.

FIG. 3 shows another obturator 30 utilizable in an endotracheal tube assembly for facilitating the placement of the tube (e.g., tube 22 in FIG. 2). Obturator 30 is provided at a distal end with an enlarged hollow head 32 provided with an L-shaped slot 34 for receiving a protuberance 36 on an indicator member 38 during insertion of the indicator member into head 32. Indicator member 38 carries a colorimetric carbon dioxide indicator strip 40.

In placing endotracheal tube 22 with obturator 24 or 30, the endotracheal tube is inserted into a patient's trachea. Obturator 24 or 30 and tube 22 are manipulated from outside the patient's body to effectuate a placement of the tube so that a distal end of the tube is positioned in the patient'lung. Upon a placement of tube 22 with obturator 24 or 30, the obturator is withdrawn from tube 22. Colorimeteric carbon dioxide indicator strip 26 or 40 is then inspected to determine whether a distal end of tube 22 is properly placed in the patient's lung. A color change of indicator strip 26 or 40 indicates proper placement.

If it is determined via the color of indicator strip 26 or 40 that tube 22 is improperly placed, tube 22 is removed and again inserted into the patient's trachea. Alternatively, a new tube may be employed. A reinsertion of the original endotracheal tube 22 may be implemented with the same obturator 24 or 30 and indicator strip 26 or 40, provided that the color thereof has not changed so much as to render the strip useless for further determinations. Alternatively, in the case of obturator 30, a new indicator member 38 may be attached to the distal end of obturator 30. In the case that the color of strip 26 of obturator 24 has changed too much for re-use, a new obturator may be used.

It is to be noted that, in contrast to the embodiments of FIGS. 2 and 3, the embodiment of FIG. 1 requires that the obturator 12 is somewhat thinner than the inner diameter of endotracheal tube 20 to allow exhaled gases to escape through the tube and around indicator strip 18 at the proximal end of obturator 12. The endotracheal obturators 24 and 30 of FIGS. 2 and 3 may snugly fit inside endotracheal tube 22. Accordingly, the embodiments of FIGS. 2 and 3 are preferred over the embodiment of FIG. 1.

Moreover, obturator 24 of FIG. 2 is preferred to obturator 30 of FIG. 3 insofar as indicator 26 is permanently attached to the distal end of the obturator, thereby ensuring that the indicator is not inadvertantly dislodged during use and lost in the trachea or the lung. Obturator 24 may be sold separately in its own disposable sterile wrapper.

Although the invention has been described in terms of particular embodiments and applications, one of ordinary skill in the art, in light of this teaching, can generate additional embodiments and modifications without departing from the spirit of or exceeding the scope of the claimed invention. It is to be noted that the particular structure for releasably locking a colorimetric indicator member to an endotracheal tube obturator may take any of a number of equivalent forms. For example, a force lock fit or a snap-lock detent are substitutable for L-shaped slot 34 and protuberance 36. A colorimetric indicator strip in accordance with the present invention may be enclosed by a semipermeable membrane for preventing particles of the indicator from entering air passing through the endotracheal tube while enabling penetration of carbon dioxide molecules to the indicator. Of course, replaceable indicator members 16 and 38 may be enclosed by separate sterile packages for shipment and handling prior to use during surgery.

Accordingly, it is to be understood that the drawings and descriptions herein are profferred by way of example to facilitate comprehension of the invention and should not be construed to limit the scope thereof.

What is claimed is:

1. An endotracheal assembly comprising:
    an endotracheal tube;
    a malleable obturator inside said tube for enabling a placement of a distal end of said tube into a patient's trachea;
    colorimeteric carbon dioxide indicator means mounted to said obturator for determining a passage of carbon dioxide through said tube upon a placement of said tube in the patient, said indicator means being removably mounted to a distal end of said obturator for determining the presence of carbon dioxide at a distal end of said tube; and
    means for releasably locking said indicator means to the distal end of said obturator.

2. The assembly defined in claim 1 wherein said tube, said obturator and said indicator means are sterile, further comprising a removable disposable wrapper enclosing said tube and said obturator for purposes of maintaining said tube, said obturator and said indicator means in a sterile condition.

3. The assembly defined in claim 1 wherein said indicator means takes the form of a cylindrical strip surrounding a portion of said obturator.

4. A device for determining proper placement of an endotracheal tube, comprising:
    a malleable obturator insertable inside the endotracheal tube;
    colorimeteric carbon dioxide indicator means mounted to said obturator for determining a passage of carbon dioxide through said tube upon a placement of said tube in the patient; and means for releasably locking said indicator means to said obturator.

5. The device defined in claim 4 wherein said indicator means is mounted to a distal end of said obturator for determining the presence of carbon dioxide at a distal end of said tube.

6. The device defined in claim 5 wherein said indicator means is removably attached to the distal end of said obturator.

7. The device defined in claim 4 wherein said obturator and said indicator means are sterile, further comprising a removable disposable wrapper enclosing said obturator for purposes of maintaining said obturator and said indicator means in a sterile condition.

8. The device defined in claim 4 wherein said indicator means takes the form of a cylindrical strip surrounding a portion of said obturator.

9. A method for placing an endotracheal tube, comprising the steps of:
providing an endotracheal tube longitudinally traversed at least partially by an obturator made of a malleable material and having a colorimeteric carbon dioxide indicator element mounted to a distal end of said obturator;
initially inserting said endotracheal tube into a patient's trachea;
manipulating said tube and said obturator of effectuate a placement of said tube;
upon a placement of said tube with said obturator, withdrawing said obturator; and
inspecting said colorimeteric carbon dioxide indicator element to determine whether a distal end of said tube is properly placed in the patient.

10. The method defined in claim 9, further comprising the steps of:
removing said tube upon determining, via a color of said indicator element, that said tube is improperly placed; and
again inserting into the patient's trachea an endotracheal tube longitudinally traversed at least partially by an obturator made of a malleable material.

11. The method defined in claim 10 wherein the obturator utilized in said step of again inserting is a different obturator than that obturator used in said step of initially inserting.

12. The method defined in claim 10 wherein the endotracheal tube utilized in said step of again inserting is the same tube used in said step of initially inserting.

13. The method defined in claim 10 wherein the endotracheal tube and obturator utilized in said step of again inserting are the same tube and obturator used in said step of initially inserting.

14. The method defined in claim 9, further comprising the step of leaving said endotracheal tube inside the patient upon determining, via a color of said indicator element, that said tube is properly placed.

* * * * *

UNITED STATES PATENT AND TRADEMARK OFFICE
CERTIFICATE OF CORRECTION

PATENT NO. : 5,273,029
DATED : December 28, 1993
INVENTOR(S) : Peter J. Wilk and James Z. Cinberg It is certified that error appears in the above-identified patent and that said Letters Patent is hereby corrected as shown below:

Column 5, line 28, claim 9, change "of" to read --to--

Signed and Sealed this

Fourteenth Day of June, 1994

*Attest:*

BRUCE LEHMAN

*Attesting Officer*    *Commissioner of Patents and Trademarks*